(12) United States Patent
Yamaguchi et al.

(10) Patent No.: US 7,126,255 B2
(45) Date of Patent: Oct. 24, 2006

(54) PIEZOELECTRIC/ELECTROSTRICTIVE FILM-TYPE DEVICE

(75) Inventors: Hirofumi Yamaguchi, Komaki (JP); Takatoshi Nehagi, Seto (JP); Kunihiko Yoshioka, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 11/089,113

(22) Filed: Mar. 24, 2005

(65) Prior Publication Data

US 2005/0218757 A1    Oct. 6, 2005

(30) Foreign Application Priority Data

Apr. 5, 2004   (JP) ............................. 2004-111468

(51) Int. Cl.
*H01L 41/047* (2006.01)
(52) U.S. Cl. .................. 310/324; 310/320; 310/365; 310/366
(58) Field of Classification Search ................ 310/320, 310/324, 365, 366
See application file for complete search history.

(56) References Cited

U.S. PATENT DOCUMENTS

| | | | |
|---|---|---|---|
| 5,235,240 A * | 8/1993 | Morita et al. ............... | 310/365 |
| 5,545,461 A | 8/1996 | Takeuchi et al. | |
| 5,889,351 A | 3/1999 | Okumura et al. | |
| 6,348,115 B1 | 2/2002 | Takeuchi et al. | |
| 6,424,237 B1 * | 7/2002 | Ruby et al. ................. | 333/187 |
| 6,541,895 B1 | 4/2003 | Yamaguchi | |
| 6,729,184 B1 * | 5/2004 | Tsukada et al. ............ | 73/290 V |
| 2003/0057806 A1 * | 3/2003 | Peczalski .................... | 310/324 |
| 2005/0110369 A1 * | 5/2005 | Onishi et al. ............... | 310/320 |
| 2006/0113879 A1 * | 6/2006 | Ren et al. .................... | 310/366 |

FOREIGN PATENT DOCUMENTS

| | | |
|---|---|---|
| JP | 08-201265 | 8/1996 |
| JP | 2002-261347 | 9/2002 |

OTHER PUBLICATIONS

U.S. Appl. No. 11/282,013, filed Nov. 17, 2005, Nanataki et al.
U.S. Appl. No. 11/281,645, filed Nov. 17, 2005, Nanataki et al.

* cited by examiner

*Primary Examiner*—Thomas M. Dougherty
(74) *Attorney, Agent, or Firm*—Burr & Brown

(57) ABSTRACT

A piezoelectric/electrostrictive film-type device is provided which includes a ceramic substrate having a thin diaphragm portion and a peripheral thick portion, a lower electrode, an auxiliary electrode, a piezoelectric/electrostrictive film, and an upper electrode. The lower electrode, the auxiliary electrode, the piezoelectric/electrostrictive film, and the upper electrode are layered in that order on the ceramic substrate. The upper electrode has a length of 30 to 70% relative to the length of the thin diaphragm portion, and preferably has a width of 70% or more relative to the width of the thin diaphragm portion.

2 Claims, 6 Drawing Sheets

— IDEAL VIBRATION DEFORMATION SHAPE

— IDEAL VIBRATION DEFORMATION SHAPE

PIEZOELECTRIC/ELECTROSTRICTIVE FILM-TYPE DEVICE

BACKGROUND OF THE INVENTION

1. Field of the Invention

The present invention relates to a piezoelectric/electrostrictive film-type device. More particularly, the present invention relates to a piezoelectric/electrostrictive film-type device used for an actuator utilizing bending displacement such as a microphone or sensors for sensing fluid properties, sound pressure, microgravity, acceleration, or the like, such as a viscosity sensor.

2. Description of Related Art

Piezoelectric/electrostrictive film-type devices have been conventionally used as an actuator or a sensor. A piezoelectric/electrostrictive film-type device used as a sensor is utilized for measuring fluid properties such as density, concentration, or viscosity, as disclosed in JP-A-8-201265, for example. This type of device is used as a sensor by utilizing the correlation between the amplitude of a piezoelectric vibrator and the viscous resistance of a fluid which comes in contact with the vibrator.

In general, the vibration mode in a mechanical system such the as vibration of a vibrator, may be replaced with an equivalent circuit in an electrical system. A piezoelectric/electrostrictive film-type vibrator is caused to vibrate in a fluid, and the vibrator is subjected to mechanical resistance based on the viscous resistance of the fluid. This allows the detection of a change in the electrical constant of the equivalent circuit of a piezoelectric which makes up the vibrator, whereby fluid properties such as viscosity, density, or concentration can be measured. A measurable fluid refers to liquid and gas, and not only includes a single-component liquid such as water, alcohol, and oil, but also includes a liquid, slurry, and paste in which a medium soluble or insoluble in a liquid such as mentioned above is mixed or suspended therein.

As the detection target electrical constant, a loss factor, phase, resistance, reactance, conductance, susceptance, inductance, capacitance, and the like can be given. In particular, a loss factor or phase having one maximum or minimum change point near the resonance frequency of the equivalent circuit is preferably used. Not only fluid viscosity, but also density or concentration can be measured thereby. For example, the sulfuric acid concentration in a sulfuric acid aqueous solution can be measured. As the index for detecting a change in the vibration mode, a change in the resonance frequency may be used instead of the electrical constant if acceptable from the viewpoint of measurement accuracy and durability.

In this type of piezoelectric/electrostrictive film-type device, as disclosed in JP-A-2002-26 1347, an auxiliary electrode 8 is formed at a position independent of a lower electrode 4 layered on a ceramic substrate 1 including a thin diaphragm portion 3 and a peripheral thick portion 2 as shown in FIG. 1 so that a part of the auxiliary electrode is positioned under a part of a piezoelectric/electrostrictive film 5. This configuration enables an upper electrode 6 to be continuously formed on the auxiliary electrode 8 and the piezoelectric/electrostrictive film 5 without breaking, whereby connection reliability of the upper electrode 6 is improved. In FIG. 1, a measurement target fluid is introduced into a cavity portion 10 through a through-hole 9. Stable device characteristics and a device which can be applied under any use conditions can be obtained by continuously forming the auxiliary electrode 8 from the thin diaphragm portion 3 to the thick portion 3.

SUMMARY OF THE INVENTION

In a sensor device which senses fluid properties by detecting the electrical characteristics derived from vibration, when such a sensor is used for detecting a change in the resonance frequency by the phase peak, it is desirable as a sensor device having high resolution and sensitivity that the phase peak is sharp at the resonance frequency as shown in FIG. 2. However, since sufficient peak sharpness cannot be obtained in a conventional device, a problem occurs when performing highly accurate detection.

In the conventional piezoelectric/electrostrictive film-type device shown in FIG. 1, the actual vibration deformation shape differs to a large extent from the ideal vibration deformation shape as shown in FIG. 4. This leads to the detection of various noises from the measurement target fluid, whereby a sharp change in the electrical characteristics cannot be obtained.

The present invention has been made to cope with the above-described problems. Specifically, an objective of the present invention is to provide a piezoelectric/electrostrictive film-type device which allows the actual vibration deformation shape to coincide with the ideal vibration deformation shape. Another objective of the present invention is to provide a sensor device having high sensitivity by using the piezoelectric/electrostrictive film-type device.

Specifically, a piezoelectric/electrostrictive film-type device according to one aspect of the present invention comprises a ceramic substrate having a thin diaphragm portion and a peripheral thick portion, a lower electrode, an auxiliary electrode, a piezoelectric/electrostrictive film, and an upper electrode, the lower electrode, the auxiliary electrode, the piezoelectric/electrostrictive film, and the upper electrode being layered on the substrate in that order, wherein a length of the upper electrode is 30 to 70% of a length of the thin diaphragm portion.

A piezoelectric/electrostrictive film-type device according to another aspect of the present invention comprises a ceramic substrate having a thin diaphragm portion and a peripheral thick portion, a lower electrode, an auxiliary electrode, a piezoelectric/electrostrictive film, and an upper electrode, the lower electrode, the auxiliary electrode, the piezoelectric/electrostrictive film, and the upper electrode being layered on the substrate in that order, wherein a width of the upper electrode is 70% or more of a width of the thin diaphragm portion.

The length of the upper electrode and the length of the thin diaphragm portion used herein means the distance between the both ends of the electrode or the diaphragm portion in the direction parallel to the lengthwise direction of the cavity portion 10, and the width of the upper electrode and the width of the thin diaphragm portion used herein means the distance between the both ends of the electrode or the diaphragm portion in the direction parallel to the widthwise direction of the cavity portion 10.

In the piezoelectric/electrostrictive film-type device according to the present invention, since the actual vibration deformation shape coincides with the ideal vibration deformation shape, a sharp change in the electrical characteristics can be obtained. This enables provision of a sensor device having higher resolution and sensitivity.

BRIEF DESCRIPTION OF THE DRAWINGS

FIG. 1 is an explanatory diagram showing an embodiment of a conventional piezoelectric/electrostrictive film-type device.

DETAILED DESCRIPTION OF THE INVENTION

A preferred embodiment of the present invention is described below. However, it should be understood that the present invention is not limited to the following embodiment, and various modifications and improvements of the design may be made within the scope of the present invention based on knowledge of a person skilled in the art.

Figure 1A:
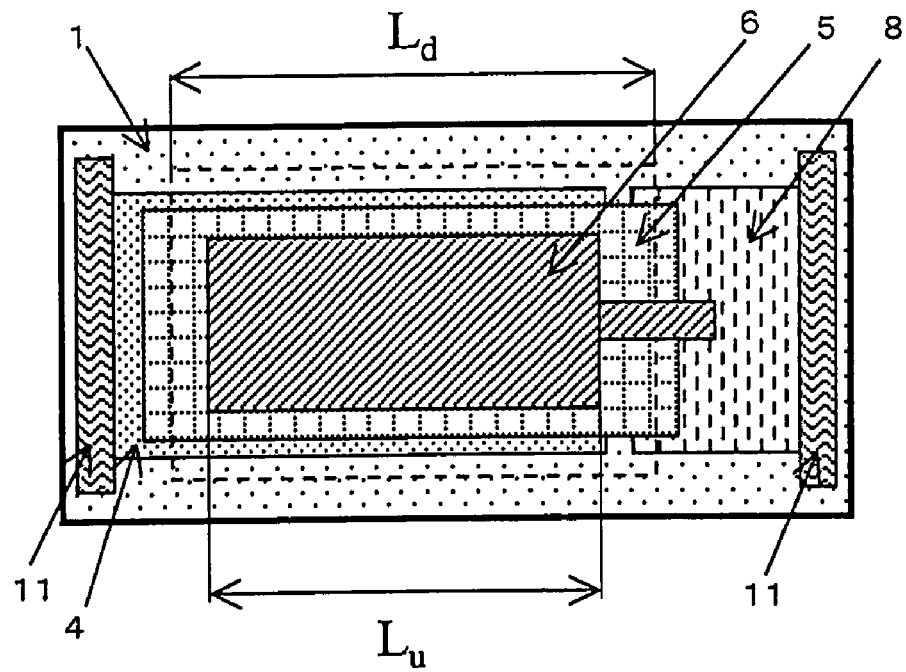
FIG. 1(a) shows a schematic plane view thereof.
Figure 1B:
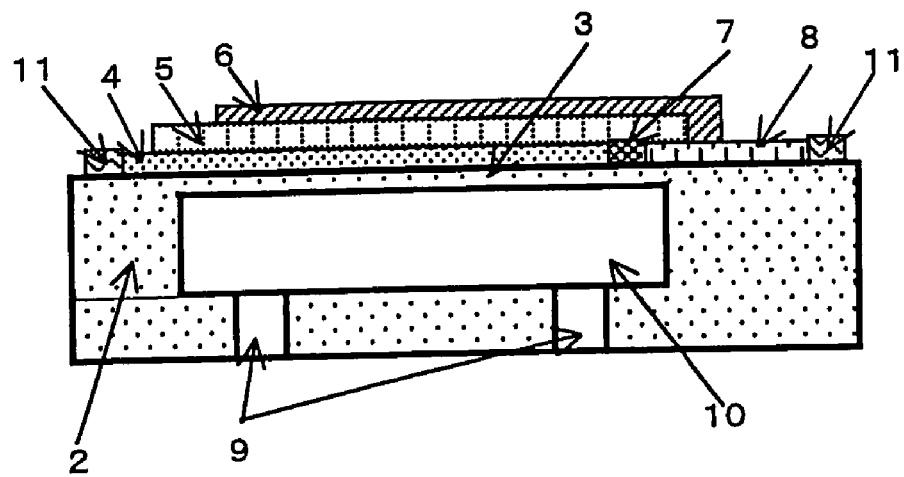
FIG. 1(b) shows a schematic cross section view thereof, respectively.

As shown in FIG. 1, a piezoelectric/electrostrictive film-type vibrator of the present invention is formed using an ordinary film forming method as a monolithic structure in which the lower electrode 4, the piezoelectric/electrostrictive film 5, and the upper electrode 6 are layered in that order on the ceramic substrate 1 including the thin diaphragm portion 3 and the thick portion 2.

The lower electrode 4 is formed to such a length that one end on the side of the auxiliary electrode 8 does not exceed the thin diaphragm portion 3. The auxiliary electrode 8 is continuously formed to have a specific length from the thick portion 1 on the side opposite to the lower electrode 4 to the thin diaphragm portion 3 so as to be placed under the piezoelectric/electrostrictive film 5 at a position independent of the lower electrode 4 on the same plane as the lower electrode 4. The piezoelectric/electrostrictive film 5 is formed to extend over the lower electrode 4 and the auxiliary electrode 8, and the upper electrode 6 is formed to extend over the piezoelectric/electrostrictive film 5 and the auxiliary electrode 8 so as to be electrically connected with the auxiliary electrode 8.

A length Lu of the upper electrode 6 is adjusted to 30 to 70% of a length Ld of the diaphragm portion 3. Since the connection portion of the upper electrode 6 for providing electrical connection with the auxiliary electrode 8 does not contribute to the substantial operation of the piezoelectric/electrostrictive film-type device, the connection portion is excluded from the length Lu.

If the length Lu exceeds 70% of the length Ld, a sharp peak cannot be obtained. If the length Lu is shorter than 30% of the length Ld, the value of the electrical constant is decreased, whereby sensitivity is decreased.

In order to obtain a sharp peak, it is preferable that the shape of the upper electrode 6 in the lengthwise direction included in the length Lu of the upper electrode 6 be line-symmetrical. This is because the symmetrical shape causes only the particular vibration to occur.

As the material for the ceramic substrate 1, a material having heat resistance, chemical stability, and insulating properties is preferable. This is because a heat treatment must be performed when integrating the lower electrode 4, the piezoelectric/electrostrictive film 5, and the upper electrode 6 as described later, and, when the piezoelectric/electrostrictive film-type device as a sensor device senses liquid properties, the liquid may exhibit conductivity or corrosiveness.

As ceramics which may be used from the above viewpoint, stabilized zirconium oxide, aluminum oxide, magnesium oxide, mullite, aluminum nitride, silicon nitride, glass, and the like can be given. Of these, stabilized zirconium oxide may be suitably used since stabilized zirconium oxide enables high mechanical strength to be maintained even when the thin diaphragm portion is formed to a small thickness and exhibits excellent toughness.

The thickness of the thin diaphragm portion 3 of the ceramic substrate 1 is generally 50 μm or less, preferably 30 μm or less, and still more preferably 15 μm or less in order that the driving amplitude of the device does not become smaller.

The surface shape of the thin diaphragm portion may be rectangular, square, triangular, elliptical, circular, or the like. In order to obtain the ideal deformation shape, the surface shape of the thin diaphragm portion is preferably rectangular, oval, or elliptical with an aspect ratio of 1.5 or more.

The lower electrode 4 and the auxiliary electrode 8 are formed on the surface of the ceramic substrate 1.

The width of the lower electrode 4 may be greater than that of the diaphragm portion 3, or may be smaller than the width of the piezoelectric/electrostrictive film 5.

The auxiliary electrode 8 is continuously formed from the end portion of the ceramic substrate 1 opposite to the lower electrode 4 to a specific position on the thin diaphragm portion 3. The end portions each of the lower electrode 4 and the auxiliary electrode 8 on the thick portion are connected with different terminal electrodes 11, respectively.

The lower electrode 4 and the auxiliary electrode 8 may be formed of either different materials or the same material. A conductive material having excellent bondability with the ceramic substrate 1 and the piezoelectric/electrostrictive film 5 is used.

In more detail, an electrode material containing platinum, palladium, rhodium, silver, or an alloy of these elements as the major component is preferably used. In particular, in the case where a heat treatment for firing is performed when forming the piezoelectric/electrostrictive film, platinum or an alloy containing platinum as the major component is preferably used.

The lower electrode 4 and the auxiliary electrode 8 are formed by using various conventional film formation methods. In more detail, a thin-film formation method such as ion beam, sputtering, vacuum deposition, CVD, ion plating, or plating, or a thick-film formation method such as screen printing, spraying, or dipping is arbitrarily selected. Of these, a sputtering method and a screen printing method are preferably selected.

When providing a bonding layer for bonding the piezoelectric/electrostrictive film 5 and the thin diaphragm portion 3 at the gap between the lower electrode 4 and the auxiliary electrode 8, as shown in FIG. 1, a bonding layer 7 is formed prior to the formation of the piezoelectric/electrostrictive film 5.

The addition of the bonding layer 7 achieves uniform rigidity on the diaphragm portion 3, whereby the ideal vibration deformation shape is obtained.

As the material for the bonding layer 7 formed of an insulator, an organic material or an inorganic material may be used insofar as the material has high adhesion and bondability with both the piezoelectric/electrostrictive film 5 and the ceramic substrate 1.

It is preferable that the material used for the bonding layer 7 has a coefficient of thermal expansion between the coefficient of thermal expansion of the substrate material and the coefficient of thermal expansion of the material for the piezoelectric/electrostrictive film 5, since highly reliable bondability is obtained. In the case where the piezoelectric/electrostrictive film 5 is subjected to heat treatment for firing, a material in which a very small amount of a glass component is added to the material used for the piezoelectric/electrostrictive film 5, or a glass material having a softening point equal to or higher than the heat treatment temperature for the piezoelectric/electrostrictive film 5 is preferably used as the material for forming the bonding layer 7 due to high adhesion and bondability with both the piezoelectric/electrostrictive film 5 and the ceramic substrate 1.

In the case where the piezoelectric/electrostrictive film 5 is formed of $(Bi_{0.5}Na_{0.5})TiO_3$ or a material containing $(Bi_{0.5}Na_{0.5})TiO_3$ as the major component, or formed of $(1-x)(Bi_{0.5}Na_{0.5})TiO_3\text{-}x\ KNbO_3$ (x is a molar fraction, $0 \leq x \leq 0.06$) or a material containing $(1-x)(Bi_{0.5}Na_{0.5})TiO_3\text{-}x\ KNbO_3$ as the major component as described later, the bonding layer 7 in which a very small amount of glass component is added to a material containing $(1-x)(Bi_{0.5}Na_{0.5})TiO_3\text{-}x\ KNbO_3$ (x is a molar fraction, $0 < x < 0.5$) as the major component is preferably used, since the bonding layer 7 exhibits high adhesion to both the piezoelectric/electrostrictive film 5 and the ceramic substrate 1 and reduces an adverse effect on the piezoelectric/electrostrictive film 5 and the substrate 1 during the heat treatment.

Specifically, since the bonding layer 7 has the same components as those of the piezoelectric/electrostrictive film 5 by forming the bonding layer 7 using $(1-x)(Bi_{0.5}Na_{0.5})TiO_3\text{-}x\ KNbO_3$ (x is a molar fraction, $0 < x < 0.5$) to which a very small amount of glass component is added, the bonding layer 7 exhibits high adhesion to the piezoelectric/electrostrictive film 5, reduces the occurrence of problems caused by the diffusion of hetero-elements which tends to occur when using only glass, and has high reactivity with the substrate 1 due to the inclusion of $KNbO_3$, whereby strong bonding can be achieved. In the case where $(1-x)(Bi_{0.5}Na_{0.5})TiO_3\text{-}x\ KNbO_3$ (x is a molar fraction, $0.08 \leq x \leq 0.5$) is used as the major component of the bonding layer, since the bonding layer shows piezoelectric characteristics to only a small extent and does not produce vibration, displacement, and stress caused by the electric field occurring between the lower electrode 4 and the auxiliary electrode 8 during use, stable device characteristics can be obtained.

A conventional thick-film formation method is used to form the bonding layer 7. In particular, a stamping method, a screen printing method, or, when the size of the area to be formed is about several tens to several hundreds microns, an inkjet method is preferably used. In the case where the heat treatment for the bonding layer 7 is necessary, the bonding layer 7 may be subjected to the heat treatment before forming the piezoelectric/electrostrictive film 5, or may be subjected to the heat treatment together with the piezoelectric/electrostrictive film 5 after forming the piezoelectric/electrostrictive film 5.

The piezoelectric/electrostrictive film 5 is formed to extend over the lower electrode 4, the auxiliary electrode 8, and the bonding layer 7. As the material for the piezoelectric/electrostrictive film, a material which exhibits a piezoelectric/electrostrictive effect may be arbitrarily used. As such a material, a lead-containing ceramic piezoelectric/electrostrictive material such as lead zirconate, lead titanate, and lead zirconate titanate (PZT), a barium titanate-containing ceramic ferroelectric such as barium titanate and a material containing barium titanate as the major component, a polymer piezoelectric such as polyvinylidene fluoride (PVDF), a Bi-containing ceramic piezoelectric such as $(Bi_{0.5}Na_{0.5})TiO_3$, and a Bi-layered ceramic can be given. A mixture and a solid solution of these materials having improved piezoelectric/electrostrictive characteristics and materials in which an additive is added to these materials may also be used.

A PZT-type piezoelectric has excellent piezoelectric characteristics and is preferably used as a material for a sensor capable of performing highly sensitive detection. In the present invention, a material containing at least one compound selected from lead titanate, lead zirconate, lead magnesium niobate, and lead nickel niobate as the major component is still more preferably used, since such a material has low reactivity with the material for the substrate, rarely allows segregation of the components to occur during the heat treatment, and enables a treatment for maintaining the composition to be performed favorably, whereby the target composition and crystal structure can be easily obtained.

In the case where platinum or an alloy containing platinum as the major component is used for the lower electrode 4 and the auxiliary electrode 8, $(Bi_{0.5}Na_{0.5})TiO_3$ or a material containing $(Bi_{0.5}Na_{0.5})TiO_3$ as the major component is preferably used, since such a material has higher bondability with platinum or an alloy containing platinum as the major component and reduces the device characteristic variation, whereby high reliability can be obtained. Of these, $(1-x)(Bi_{0.5}Na_{0.5})TiO_3\text{-}x\ KNbO_3$ (x is a molar fraction, $0 \leq x \leq 0.06$) or a material containing $(1-x)(Bi_{0.5}Na_{0.5})TiO_3\text{-}x\ KNbO_3$ as the major component is still more preferably used due to comparatively high piezoelectric characteristics.

Such a piezoelectric/electrostrictive material is formed into the piezoelectric/electrostrictive film 5 by using various conventional film formation methods in the same manner as the lower electrode 4 and the auxiliary electrode 8. In particular, screen printing is preferably used from the viewpoint of reduction in cost.

The resulting piezoelectric/electrostrictive film 5 is optionally subjected to a heat treatment, and is integrated with the lower electrode 4, the auxiliary electrode 8, and the bonding layer 7. In the case where it is necessary to increase the bondability of the piezoelectric/electrostrictive film 5 with the lower electrode 4, the auxiliary electrode 8, and the bonding layer 7 in order to reduce the device characteristic variation and increase reliability, it is preferable to use $(Bi_{0.5}Na_{0.5})TiO_3$ or a material containing $(Bi_{0.5}Na_{0.5})TiO_3$ as the major component, in particular, $(1-x)(Bi_{0.5}Na_{0.5})TiO_3\text{-}x\ KNbO_3$ (x is a molar fraction, $0 \leq x \leq 0.06$) or a material containing $(1-x)(Bi_{0.5}Na_{0.5})TiO_3\text{-}x\ KNbO_3$ as the major component, and to subject the piezoelectric/electrostrictive film 5 to a heat treatment at a temperature of 900 to 1400° C., and preferably 1000 to 1300° C. This also applies to the case of using a PZT-type material. In this case, it is preferable to perform the heat treatment while controlling the atmosphere together with the vaporization source of the piezoelectric/electrostrictive material so that the piezoelectric/electrostrictive film 5 does not become unstable at a high temperature.

The upper electrode 6 is continuously formed on the piezoelectric/electrostrictive film 5 formed as described above so as to extend from the piezoelectric/electrostrictive film 5 to the auxiliary electrode 8.

As the material for the upper electrode 6, a conductive material having high bondability with the piezoelectric/electrostrictive film 5 is used. The upper electrode 6 is formed by using a film formation method similar to that for the lower electrode 4 and the auxiliary electrode 8.

The upper electrode 6 is optionally subjected to a heat treatment after film formation, and is bonded to the piezoelectric/electrostrictive film 5 and the auxiliary electrode 8 to form a monolithic structure. The heat treatment is not necessarily required as described for the lower electrode 4.

In order to obtain the ideal deformation shape, it is preferable that the rigidity be uniform on the diaphragm portion 3. Therefore, it is preferable to integrate the lower electrode 4, the auxiliary electrode 8, the piezoelectric/electrostrictive film 5, and the upper electrode 6 with the diaphragm portion 3 by performing a heat treatment rather than bonding the lower electrode 4, the auxiliary electrode 8, the bonding layer 7, the piezoelectric/electrostrictive film 5, and the upper electrode 6 using an adhesive.

The length Lu of the upper electrode 6 is adjusted to 30 to 70% of the length Ld of the diaphragm portion 3. In order to obtain the ideal deformation shape, the width of the upper electrode 6 is adjusted to 70% or more of the width of the diaphragm portion 3. In the case of comparing the width of the upper electrode 6 with the width of the diaphragm portion 3, the comparison should be made between the portions having the greatest width of the respective members.

In order to obtain a sharp peak, it is preferable that the shape of the upper electrode 6 in the widthwise direction be line-symmetrical. This is because the symmetrical shape causes only the particular vibration to occur.

It is preferable that the center of the upper electrode 6 coincide with the center of the diaphragm portion 3. If the difference between the center of the upper electrode 6 and the center of the diaphragm portion 3 is 5% or less of the length of the diaphragm portion 3 in the lengthwise direction of the diaphragm portion 3 and is 10% or less of the width of the diaphragm portion 3 in the widthwise direction, there is no problem since the ideal deformation shape can be obtained.

It is preferable that the ratio of the area of the portion of the upper electrode 6 which contributes to the operation to the area of the diaphragm portion 3 be 15% or more, but 40% or less. If the ratio is 15% or more, vibration necessary for sensing can be obtained. If the ratio is 40% or less, rigidity advantageous for vibration can be obtained.

Figure 5:
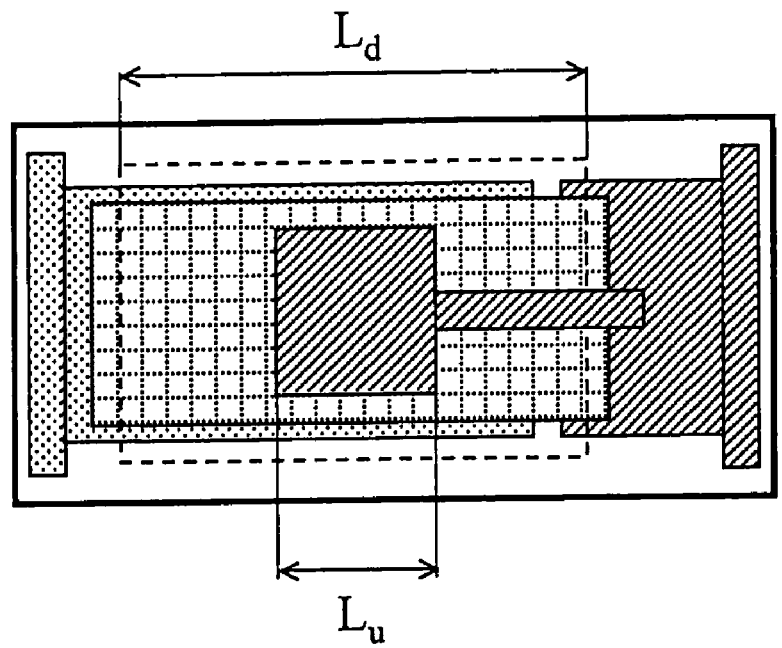
FIG. 5 is an explanatory diagram showing an embodiment of a piezoelectric/electrostrictive film-type device according to the present invention.
Figure 6:
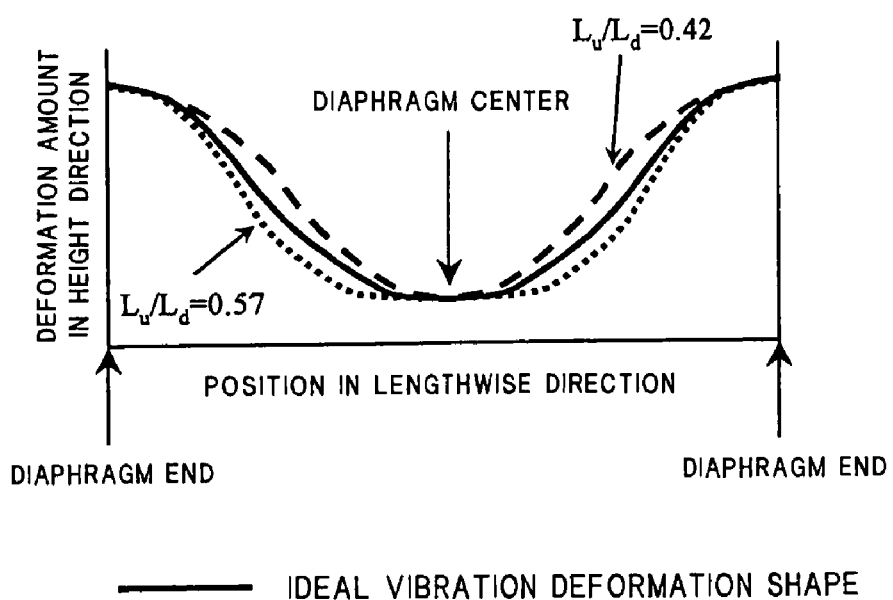
FIG. 6 is an explanatory diagram showing the vibration deformation shape in FIG. 5.

FIG. 5 shows a piezoelectric/electrostrictive film-type sensor device as an example of the present invention. FIG. 6 shows the actual vibration deformation shape when the upper electrode was formed in a rectangular shape and Lu/Ld was set at 0.42 and 0.57 (Example 1).

Figure 2:
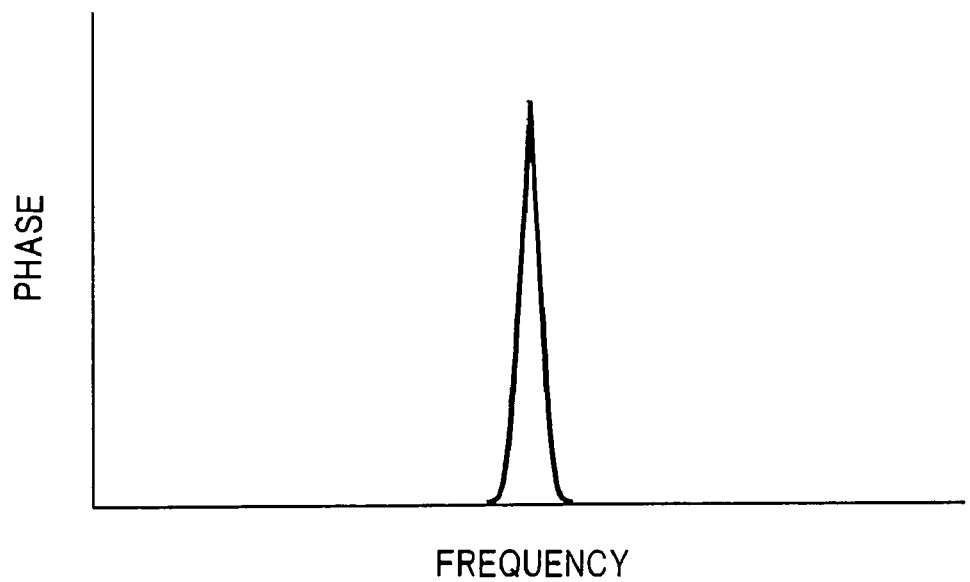
FIG. 2 is an explanatory diagram showing a peak shape desirable as a piezoelectric/electrostrictive film-type device.
Figure 3:
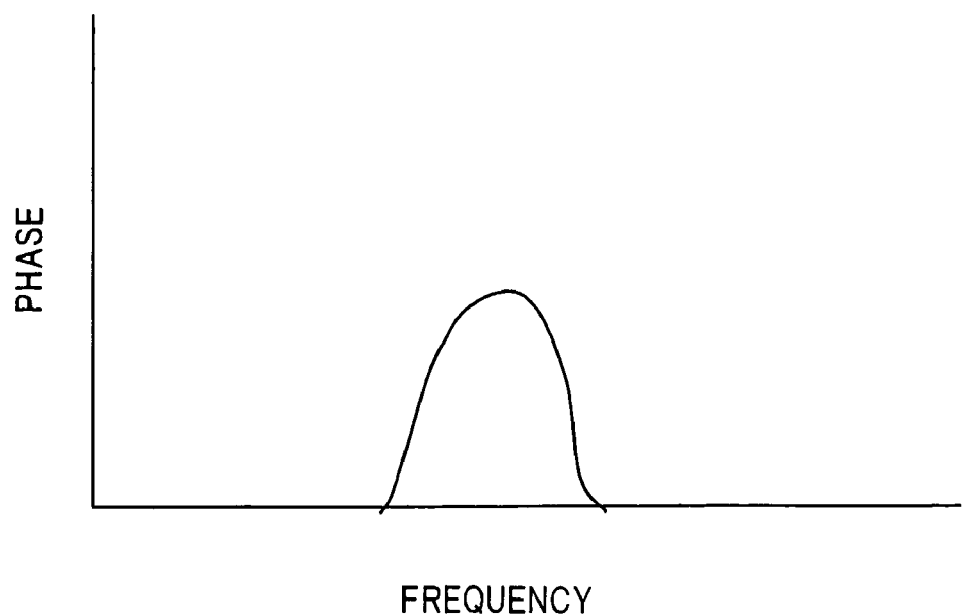
FIG. 3 is an explanatory diagram showing a peak shape of a conventional piezoelectric/electrostrictive film-type device.
Figure 4:
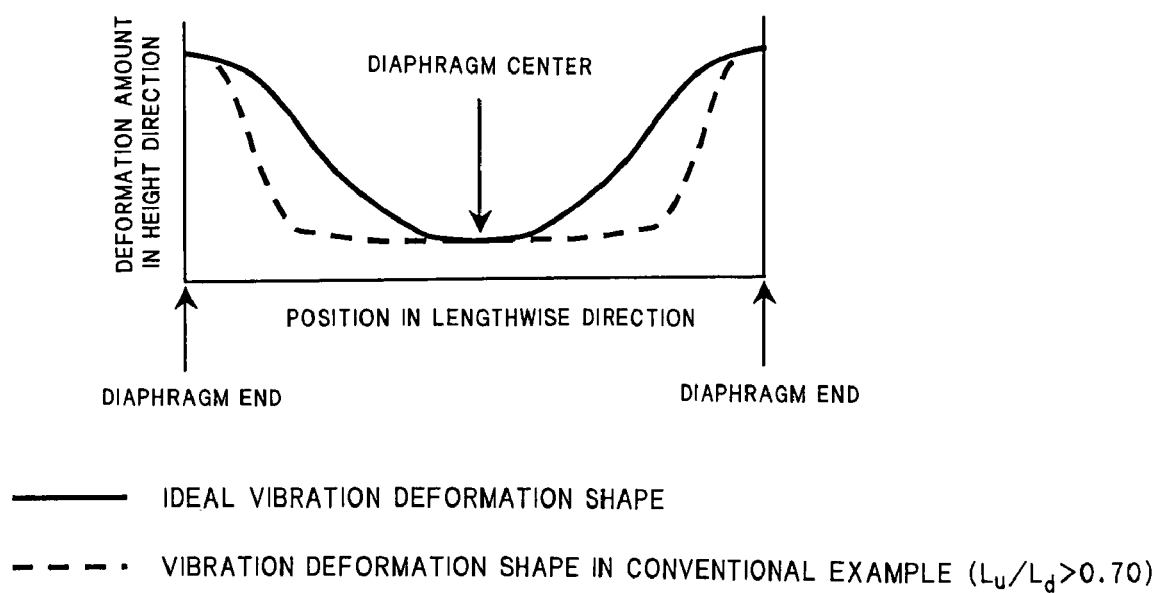
FIG. 4 is an explanatory diagram showing a conventional vibration deformation shape.

As is clear from FIG. 5, the resulting vibration deformation shape was close to the ideal vibration deformation shape. The phase peak of the device with respect to the frequency was as shown in FIG. 2 to obtain a sharp peak.

Figure 7:
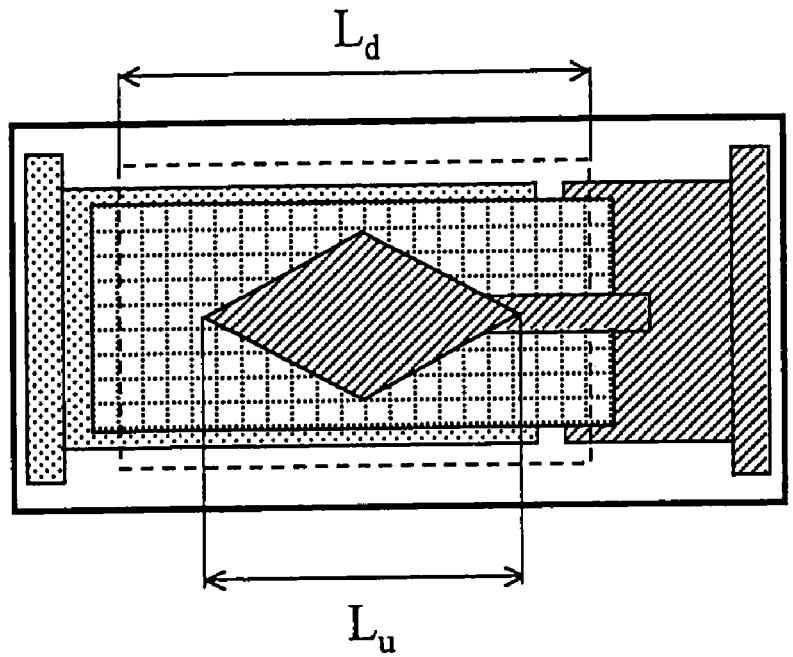
FIG. 7 is an explanatory diagram showing another embodiment of a piezoelectric/electrostrictive film-type device according to the present invention.
Figure 8:
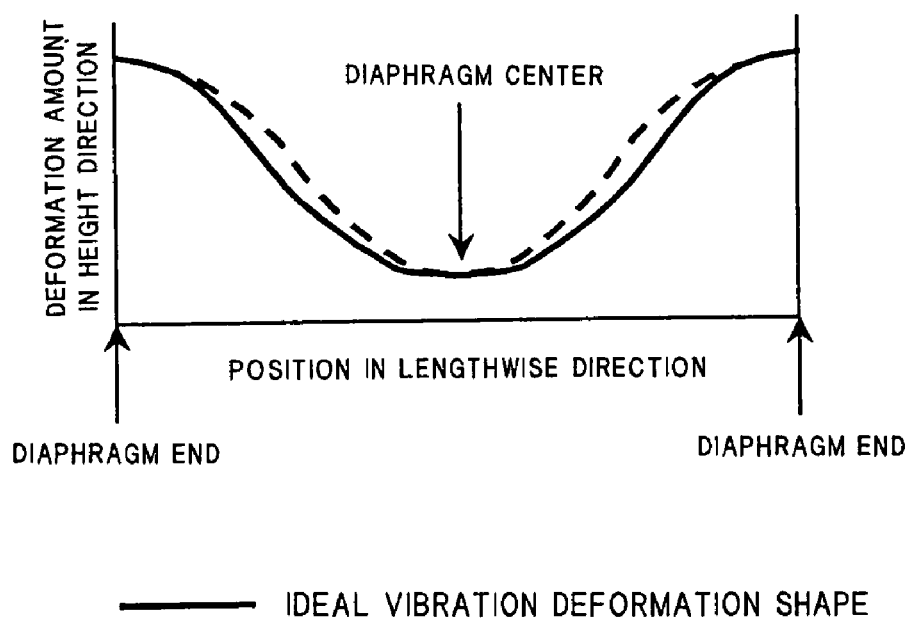
FIG. 8 is an explanatory diagram showing the vibration deformation shape in FIG. 7.

When the upper electrode was formed in a diamond shape and Lu/Ld was set at 0.57 (Example 2) as shown in FIG. 7, the actual vibration deformation shape was close to the ideal vibration deformation shape as shown in FIG. 8. The phase peak of the device with respect to the frequency was as shown in FIG. 2 to obtain a sharp peak.

Figure 9:
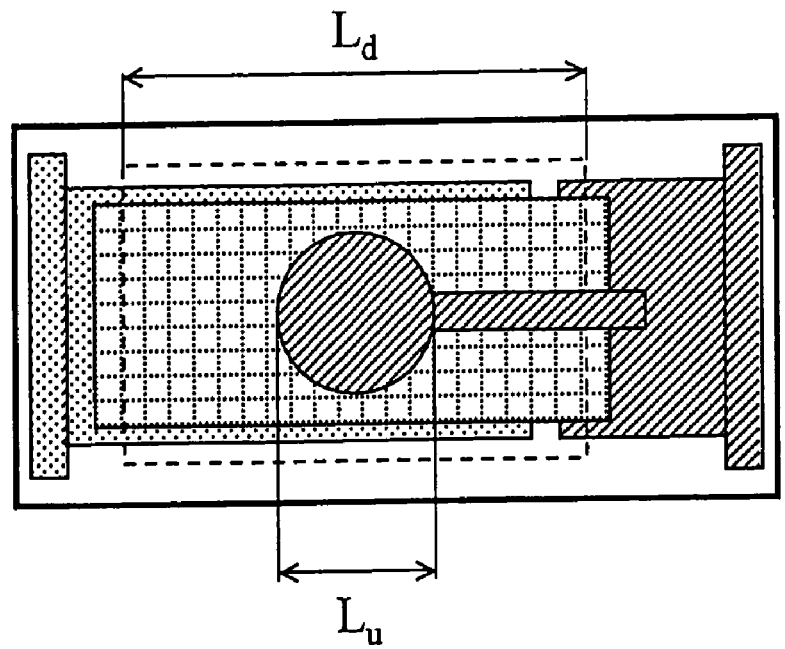
FIG. 9 is an explanatory diagram showing yet another embodiment of a piezoelectric/electrostrictive film-type device according to the present invention.
Figure 10:
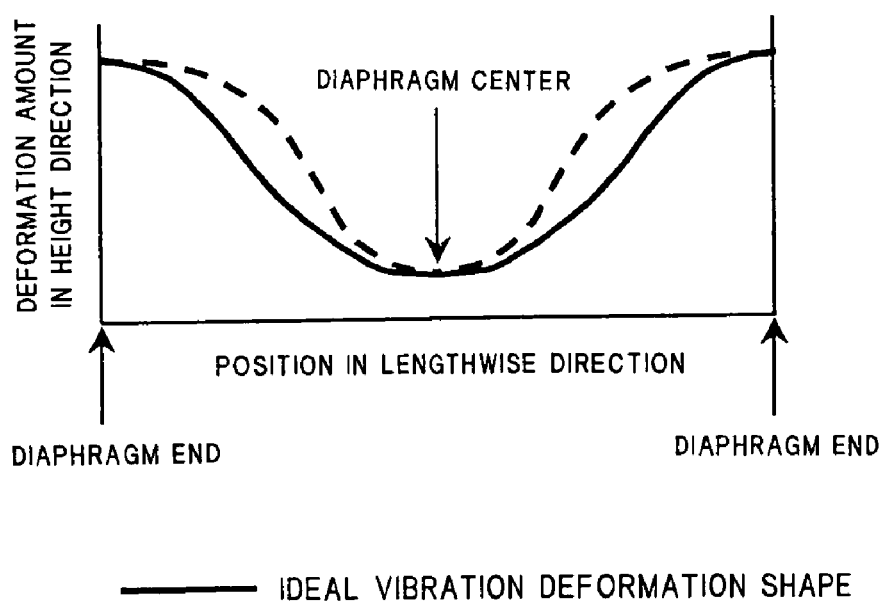
FIG. 10 is an explanatory diagram showing the vibration deformation shape in FIG. 9.

When the upper electrode was formed in a circular shape and Lu/Ld was set at 0.42 (Example 3) as shown in FIG. 9, the actual vibration deformation shape was close to the ideal vibration deformation shape in comparison with a conventional example, as shown in FIG. 10. The phase peak of the device with respect to the frequency was as shown in FIG. 2 to obtain a sharp peak.

In the case where the lower electrode 4, the bonding layer 7, the piezoelectric/lectrostrictive film 5, and the upper electrode 6 are bonded by performing a heat treatment, the heat treatment may be performed each time these components are formed, or these components may be subjected to the heat treatment at the same time after forming each component. The heat treatment temperature is appropriately selected in order to ensure excellent bondability and to prevent a change in properties due to diffusion of constituent elements during the heat treatment.

In FIG. 1, the through-hole 9 is provided to the cavity portion 10. However, the structure under the cavity portion in which the device comes into contact with a fluid is not limited, and a simple cavity structure without a lid portion or the like may be employed.

The end portion of the piezoelectric/electrostrictive film 5 in the lengthwise direction may be disposed in such a manner that it does not exceed the thin diaphragm portion 3, and that the piezoelectric/electrostrictive film 5 does not extend over the thick portion 2 may be employed.

What is claimed is:

1. A piezoelectric/electrostrictive film-type device, comprising:
   a ceramic substrate having a thin diaphragm portion and a peripheral thick portion, a lower electrode, an auxiliary electrode, a piezoelectric/electrostrictive film, and an upper electrode; the lower electrode, the auxiliary electrode, the piezoelectric/electrostrictive film, and the upper electrode being layered on the substrate in that order,
   wherein a length of the upper electrode is 30 to 70% of a length of the thin diaphragm portion.

2. A piezoelectric/electrostrictive film-type device according to claim 1, wherein a width of the upper electrode is 70% or more of a width of the thin diaphragm portion.

* * * * *